United States Patent [19]

Borsotti

[11] Patent Number: 5,371,299
[45] Date of Patent: Dec. 6, 1994

[54] PROCESS FOR THE PREPARATION OF DIETHERS

[75] Inventor: Giampietro Borsotti, Novara, Italy

[73] Assignee: Himont Incorporated, Wilmington, Del.

[21] Appl. No.: 15,330

[22] Filed: Feb. 9, 1993

Related U.S. Application Data

[63] Continuation of Ser. No. 794,553, Nov. 19, 1991, abandoned.

[30] Foreign Application Priority Data

Nov. 20, 1990 [IT] Italy .................. 22119 A/90

[51] Int. Cl.⁵ .............................. C07C 41/00
[52] U.S. Cl. .................... 568/672; 568/461; 568/463; 568/660; 568/662; 568/664; 568/670
[58] Field of Search ............... 568/461, 463, 660, 662, 568/664, 670, 672

[56] References Cited

U.S. PATENT DOCUMENTS

| | | | |
|---|---|---|---|
| 3,742,068 | 6/1973 | Moersch et al. | 568/672 |
| 3,752,843 | 8/1973 | Henrick et al. | 260/465.9 |
| 4,263,460 | 4/1981 | Weber et al. | 568/457 |
| 4,317,945 | 3/1982 | Bernhagen et al. | 568/461 |
| 4,435,586 | 3/1984 | Kruse et al. | 549/464 |
| 5,095,153 | 3/1992 | Agnes et al. | |

FOREIGN PATENT DOCUMENTS

| | | |
|---|---|---|
| 0361493 | 4/1990 | European Pat. Off. |
| 731917 | 6/1955 | United Kingdom |

OTHER PUBLICATIONS

Astle et al, Industrial and Engineering Chemistry, Aldol Condensation, 44:12 (1952) 2869–2872.

*Primary Examiner*—Johann Richter
*Assistant Examiner*—Rebecca Cook

[57] ABSTRACT

Preparation of diethers of the formula

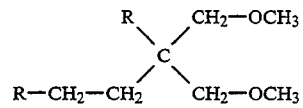

wherein R is an alkyl, cycloalkyl, aryl, or aralkyl radical, by formation of an unsaturated aldehyde of the formula

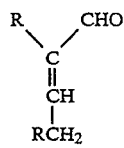

wherein R is as defined above, by means of an aldol condensation reaction, reduction of said aldehyde to form the corresponding saturated compound, transformation of the saturated compound into the corresponding diol, and consequent methylation of the diol into diether.

4 Claims, No Drawings

PROCESS FOR THE PREPARATION OF DIETHERS

This application is a continuation of application Ser. No. 07/794,553, filed Nov. 19, 1991 now abandoned.

The present invention concerns a process for the preparation of diethers of the formula

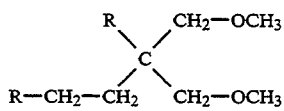
(I)

where R is a linear or branched $C_{1-18}$ alkyl, $C_{3-18}$ cycloalkyl, $C_{6-18}$ aryl or $C_{7}-C_{18}$ arylalkyl group; preferably R is isopropyl.

It is already known how to prepare diethers of the formula (I) according to methods described in published European application EP-A-361 493, corresponding to U.S. Ser. No. 413,409.

For many reasons, however, the above mentioned methods are not very adequate for commercial application.

For example, the patent application mentioned above describes the preparation of 2-isoamyl-2-isopropyl-1,3-dimethoxypropane in four steps with a total yield of 12%. Moreover, the final methylation of the diol is obtained using extremely expensive reagents.

By operating according to the method of this invention, on the other hand, one can obtain the ethers (I) in high yield with a simplified process, using unexpensive reagents.

The process of the invention comprises the following steps:
a) formation of the unsaturated aldehyde (II), wherein R is as defined above, by means of an aldol condensation reaction;
b) reduction of said aldehyde to saturated compound (III), wherein R is as defined above;
c) transformation of (III), by means of a crossed Cannizzaro reaction with formaldehyde, into the diol (IV); wherein R is as defined above;
d) methylation of the diol (IV) with $CH_3Cl$ to produce the diether (I).

The reaction is advantageously carried out in the presence of dimethyl sulfoxide (DMSO).

The reactions which occur in the process are represented as follows:

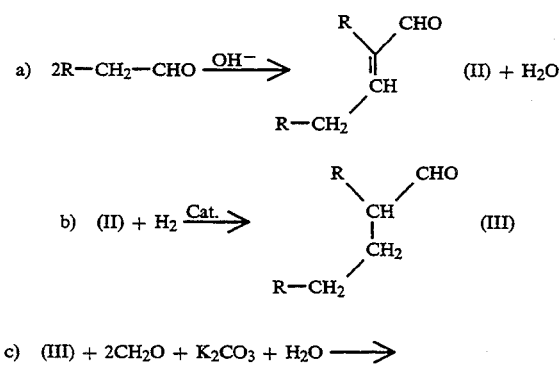

c) (III) + $2CH_2O$ + $K_2CO_3$ + $H_2O$ ⟶

-continued

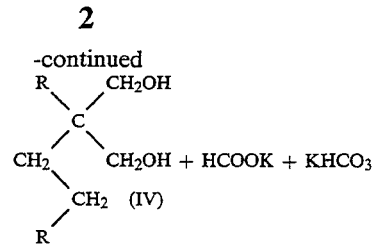

d) (IV) + $2CH_3Cl$ + 2NaOH $\xrightarrow{DMSO}$

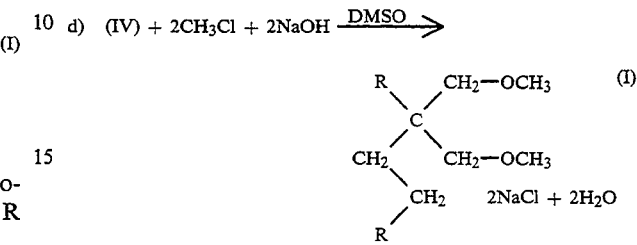
2NaCl + $2H_2O$

The aldol condensation is preferably carried out in the presence of an ion-exchange resin with an extremely basic function, for instance quaternary ammonium hydroxide. An example of such resin is Amberlite IRA 910 (produced by Rohm & Haas). It is also possible to use a resin in the form of quaternary ammonium chloride mixed with an equivalent amount of NaOH.

Operating under these conditions it is possible to limit the formation of polycondensates. In fact, as shown in Examples 2 and 3, if one uses NaOH, even when operating at very low conversions, the quantity of undesired polycondensates expressed in percentage on the aldehyde (II) obtained, are respectively 25.7% and 23.5%, compared to 5.8% of Example 1 (where the resin used was in the OH form), and 8.7% of Example 4 (where the resin used was in the form of $Cl^-+$NaOH).

The resin can be recycled repeatedly without appreciable loss of activity.

Aldehyde (II) is selectively reduced with Pd on charcoal catalyst to (III) with practically quantitative yields. Reduction times, with equal quantities of catalyst, are noticeably reduced by adding small quantities of aqueous solutions of alkaline bicarbonates. As shown in Examples 5 and 6, the reduction times after adding an aqueous saturated solution of $NaHCO_3$ go from 80 hours to 1 hour.

In the methylation of the diol (IV) the ether (I) obtained will not mix with the dimethyl sulfoxide: thus the separation and recovery of the solvent are thus simplified.

A preferred embodiment of the process of the invention is carried out in the following manner:
a) isovaleraldehyde is heated in the presence of an ion-exchange resin with basic functionality (form $OH^-$), or, as an alternative, a resin in the form of quaternary ammonium chloride with the same amount of NaOH, to a temperature between 70° C. and 120° C., removing the water continuously as it forms. The aldehyde (II) is separated from the resulting reaction mixture by means of fractional distillation;
b) (II) is hydrogenated in the presence of a solvent at room temperature and at a pressure from 1 to 10 atm, preferably from 2 to 3 atm, in the presence of a palladium based catalyst and small quantities of an aqueous solution of alkaline bicarbonate (1–10% by weight of saturated solution).

Solvents suitable for use in this process are alcohols, such as $CH_3OH$, ethanol, isopropanol and butanol. Preferably methanol and ethanol are used. The concentration of (II) in the solvent can vary from 10 to 50%, preferably it is from 15 to 20%.

Suitable catalysts are finely divided palladium, optionally supported on an inert medium, such as silica, alumina, charcoal and barium sulfate. The quantity of catalyst can vary from 0.2 to 3 g Pd/Kg of (II). The hydrogenation rate (at equal pressure and temperature) is proportional to the quantity of catalyst used. The alcohol solution of (III), after removal of the catalyst by filtration, is used directly in the following step without further purification.

c) The alcohol solution of (III) with a $CH_2O$ aqueous solution is heated in the presence of an inorganic base, and refluxed until the reaction is complete. The alcohol is recovered by distillation and the diol(IV) is separated from the aqueous phase wherein it is scarcely soluble, anhydrated and it is then used in the following step without further purification.

Bases suitable for the reaction are NaOH, KOH, $Na_2CO_3$ and $K_2CO_3$. The $CH_2O$ is added in a molar ratio of at least 2:1 with the aldehyde (III), preferably in a ratio of 3:1.

d) The unpurified diol (IV) is dissolved in DMSO and methylated with $CH_3Cl$ in the presence of NaOH, at atmospheric pressure and a temperature from 30° to 40° C. The use of finely divided NaOH is preferred, since it allows for a faster reaction.

The ether (I) is insoluble in the DMSO and after filtration of the salts, it is easily separated from the solvent and rectified. After dehydration (addition of toluene and azeotropic distillation of the toluene/$H_2O$ mixture for example), the DMSO can be recycled.

The following examples are given in order to illustrate and not limit the invention.

EXAMPLE 1

Preparation of 2-isopropyl-5-methyl-2-hexenal [II, $R=(CH_3)_2CH$]

2070 g of isovaleraldehyde and 260 cc of Amberlite IRA 910 resin (produced by Rohm & Haas) in the form of $OH^-$ (prepared from the $Cl^-$ form by washing with NaOH until no $Cl^-$ appears in the wash and then with $H_2O$ until it is neutralized) are heated in reflux.

The water that forms is continuously removed with a Marcusson distiller. After 3 hours about 260 cc of $H_2O$ are collected, and the temperature in the boiler goes from the initial 79° C. to 115° C. The resin is separated by filtration and the reaction product is fractioned under vacuum. The following products are obtained: 444 g of isovaleraldehyde which can be recycled, an intermediate fraction of 50 g, a fraction of 1300 g made up essentially (II) (boiling point 85°–90° C./20 mmHg) and 75g of nondistillable residue of polycondensate.

The gas chromatographic titre of (II) is 97% (cis and trans isomers in an approximate 20:80 ratio.).

The quantity of high boiling point by-products is 5.8% with respect to the aldehyde (II) obtained.

EXAMPLE 2

The procedure and ingredients of Example 1 are used except that 20.7 g of NaOH dissolved in 250 cc of $H_2O$ are used instead of the resin. After fractionation, 1233 g of aldehyde (II) and 317 g of residue are obtained. The percentage of residue with respect to the product (II) is 25.7%.

EXAMPLE 3

The procedure and ingredients of Example 2 are used except that 11.3 g of NaOH dissolved in 350 cc of $H_2O$ are used. The reaction mixture is maintained in reflux for 5 hours (maximum temperature of the boiler 85° C.). The organic phase is separated and distilled under vacuum. The results are 980 g of light product, mainly consisting of isovaleraldehyde, 811 g of (II) and 191 g of residue. The percentage of residue is 23.5% with respect to the desired product (II).

EXAMPLE 4

1400 g of isovaleraldehyde and 150 cc of wet Amberlite IRA 910 resin in $Cl^-$ form, and 5 g of NaOH dissolved in 100 cc of $H_2O$ are heated. They are heated in reflux distilling off, with a Marcusson apparatus, the water that forms during the process. After 3 hours the internal temperature reaches 90° C. Another 3 g of NaOH dissolved in 30 cc of $H_2O$ are added and the distillation continues again for 5 hours until a temperature of 120° C. is reached. The reaction mass is then cooled to 80° C. and diluted with 200 cc of $H_2O$. The aqueous phase and the resin are then separated, and the unpurified reaction product is distilled.

The results are 110 g of light products constituted primarily of isovaleraldehyde, 1025 g of aldehyde (II) and 90 g of residue. The percentage of residue is 8.7% with respect to the desired product (II).

EXAMPLE 5

Preparation of 2-isopropyl-5-methylhexanale (III, $R=(CH_3)_2CH-$].

Into a glass flask with two necks equipped with agitator, are introduced 10 g of the aldehyde of Example 1 dissolved in 70 cc of ethanol, 1 cc of a saturated $NaHCO_3$ aqueous solution and 0.25 g of 10% Pd on charcoal. The apparatus is fluxed with nitrogen, then with hydrogen, and connected to a graduated burette filled with hydrogen. The mixture is maintained under agitation at room pressure and temperature.

The absorption of hydrogen stops at the stoichiometric value after 60 min.

EXAMPLE 6

Example 5 is repeated, but without adding the $NaHCO_3$ solution. Absorption is complete only after 80 hours.

EXAMPLE 7

A solution of 1300 g of aldehyde [II, $R=(CH_3)_2CH_2CH$] in 7 liters of ethanol and 80 cc of saturated $NaHCO_3$ solution are hydrogenated in a 20 liters autoclave in the presence of 25 g of 10% Pd on charcoal.

The operation takes place at an initial $H_2$ pressure of 3 atm reintegrating the gas as soon as its pressure decreases to 1.5 atm. The absorption is complete after 1 hour. The catalyst is filtered and the ethanol solution is used for the next reaction. The content of aldehyde [III, $R=(CH_3)_2CH$] calculated by gas chromatography is 97%.

EXAMPLE 8

Preparation of 2-isopropyl-2-(3-methylbutyl)-1,3-dihydroxypropane [IV, $R=(CH_3)_2CH$].

The aldehyde solution of Example 7 is heated in reflux with a solution of 690 g of $K_2CO_3$ in 1700 cc of $H_2O$ and 2200 cc of CH$_2$O aqueous at 40% for 7 hours. The ethanol is distilled by bringing the temperature in the boiler at 97°–98° C. The organic phase is separated, washed with hot water until it is neutralized and the oil phase is dehydrated by means of azeotropic distillation with toluene.

After evaporating the toluene under vacuum, 1455 g of a colorless oil [IV, R=(CH$_3$)$_2$CH] are obtained.

The product does not have to be further purified and is used as is in the following reaction.

EXAMPLE 9

Preparation of 2-isopropyl-2-(3-methylbutyl-(1,3-dimethoxypropane [I, R=(CH$_3$)$_2$CH]

The diol obtained in Example 8 is dissolved in 3.5 liters of dimethyl sulfoxide in a flask equipped with a bubble valve for release of gas, a mechanical blade agitator, thermometer and tube for the introduction of gases. 460 g of finely divided NaOH are added while agitating and cooling with an external bath in order to keep the temperature from going above 30° C. CH$_3$Cl is added into the well stirred mass while maintaining the temperature between 30 and 35° C. and regulating the addition so that the CH$_3$Cl does not escape from the discharge valve. After 2.5 hours, an additional 290 g of finely divided NaOH are introduced and after 5 hours another 415 g, of said NaOH. After about 8 hours the absorption of CH$_3$Cl ceases. The total CH$_3$Cl used is 925 g. After 10 hours a gas chromatographic control of the resulting reaction mixture shows the presence of 98.8% of diether [I, R=(CH$_3$)$_2$CH] and only 0.1% of monoether. The reaction mass is filtered and the salts are washed with hexane. The upper phase is separated from the DMSO, the hexane coming from the wash is added, it is washed repeatedly with H$_2$O, and dehydrated on anhydrous Na$_2$SO$_4$. After eliminating the hexane, one obtains, from the distillation, a single fraction of 1335 g of (I), with boiling point of 105°–6° C./15 mmHg. The content of diether established by gas chromatography is 99.5%. The yield on the three stages, reduction, Cannizzaro and methylation, is 77.7%.

After azeotropic dehydration with toluene the DMSO can be recycled.

EXAMPLES 10–12

Condensation, hydrogenation, Cannizzaro condensation, and etherification reactions on the feedstock shown in table 1 are carried out, respectively, with the same process as described in Examples 1, 7, 8, and 9.

Other features, advantages and embodiments of the invention disclosed herein will be readily apparent to those exercising ordinary skill after reading the foregoing disclosure.

In this regard, while specific embodiments of the invention have been described in considerable detail, variations and modifications of these embodiments can be effected without departing from the spirit and scope of the invention as described and claimed.

TABLE 1

| Aldehyde (g) | II (g) | Aldehyde recovered (g) | III (g) | IV (g) | I (g) |
|---|---|---|---|---|---|
| CH$_3$(CH$_2$)$_2$CHO (1730) | 1000 | 370 | 980 | 1050 | 940 |
| CH$_3$(CH$_2$)$_5$CHO (2745) | 1770 | 588 | 1720 | 1900 | 1700 |
| C$_6$H$_{11}$—CH$_2$CHO | 1900 | 640 | 1850 | 2030 | 1816 |

TABLE 1-continued

| Aldehyde (g) | II (g) | Aldehyde recovered (g) | III (g) | IV (g) | I (g) |
|---|---|---|---|---|---|
| (3030) | | | | | |

I claim:

1. A process for the preparation of diethers of the formula

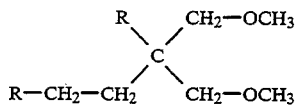

where R is a C$_{1-18}$ alkyl, a C$_{3-18}$ cycloalkyl, a C$_{6-18}$ aryl, or a C$_{7-18}$ aralkyl radical, consisting essentially of the following operations:

a) formation of an unsaturated aldehyde of the formula

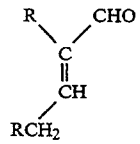

wherein R is as defined above, by means of an aldol condensation reaction, in the presence of an ion exchange resin with basic functionality or in the form of a quaternary ammonium chloride, at a temperature between 70° to 120° C.;

b) reduction of said unsaturated aldehyde to a saturated compound of the formula

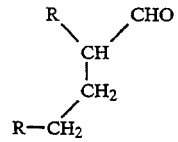

wherein R is defined above, in the presence of an alkyl alcoholic solvent, a palladium based catalyst in the amount of from 0.2 to 3 g/kg of said aldehyde and an aqueous solution of alkaline bicarbonate (1–10% by weight of saturated solution), at room temperature and pressure of from 1 to 10 atm;

c) transformation of said saturated compound into a diol of the formula

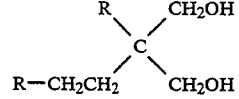

wherein R is as defined above, in the presence of an inorganic base with a CH$_2$O aqueous solution, wherein the ratio of CH$_2$O to the aldehyde is at least 2:1;

d) methylation with CH$_3$Cl in the presence of NaOH of said diol, present in DMSO, into the corresponding diether, at atmospheric pressure and a temperature of from 30° to 40° C.

2. The process of claim 1, wherein R is selected from the group consisting of isopropyl, ethyl, butyl, isobutyl, cyclohexyl, cyclopentyl.

3. The process of claim 1 wherein the aldol condensation is carried out in the presence of an ionic exchange resin with basic function, or in the form of quaternary ammonium chloride, while continuously removing water, the reduction of the unsaturated aldehyde is carried out at room temperature and from 1 to 10 arm, with hydrogen using, as a catalyst, Pd supported on an inert medium suspended in an alcoholic solution, containing minor proportions of aqueous solution of alkaline bicarbonate, and the methylation of the diol is carried out in dimethyl sulfoxide.

4. The process of claim 2 wherein the aldol condensation is carried out in the presence of an ionic exchange resin with basic function, or in the form of quaternary ammonium chloride, while continuously removing water, the reduction of the unsaturated aldehyde is carried out at room temperature and from 1 to 10 arm, with hydrogen using, as a catalyst, Pd supported on an inert medium suspended in an alcoholic solution, containing minor proportions of aqueous solution of alkaline bicarbonate, and the methylation of the diol is carried out in dimethyl sulfoxide.

* * * * *

UNITED STATES PATENT AND TRADEMARK OFFICE
CERTIFICATE OF CORRECTION

PATENT NO. : 5,371,299
DATED : December 6, 1994
INVENTOR(S) : Giampietro Borsotti It is certified that error appears in the above-identified patent and that said Letters Patent is hereby corrected as shown below:

Col. 7, line 6 and col. 8, line 6, "arm" should be --atm--

Signed and Sealed this

Eleventh Day of July, 1995

Attest:

BRUCE LEHMAN

Attesting Officer

Commissioner of Patents and Trademarks